(12) United States Patent
Harding

(10) Patent No.: US 7,486,760 B2
(45) Date of Patent: Feb. 3, 2009

(54) COMPACT SYSTEMS AND METHODS FOR GENERATING A DIFFRACTION PROFILE

(75) Inventor: Geoffrey Harding, Hamburg (DE)

(73) Assignee: GE Security, Inc., Bradenton, FL (US)

( * ) Notice: Subject to any disclaimer, the term of this patent is extended or adjusted under 35 U.S.C. 154(b) by 62 days.

(21) Appl. No.: 11/504,263

(22) Filed: Aug. 15, 2006

(65) Prior Publication Data

US 2008/0043912 A1 Feb. 21, 2008

(51) Int. Cl.
G01N 23/20 (2006.01)
(52) U.S. Cl. .............................. 378/7; 378/88
(58) Field of Classification Search ............. 378/4–20, 378/57, 70, 82, 83, 86–90, 122
See application file for complete search history.

(56) References Cited

U.S. PATENT DOCUMENTS

| | | | |
|---|---|---|---|
| 6,601,519 | B1 | 8/2003 | Bindloss, Jr. et al. |
| 6,754,300 | B2 * | 6/2004 | Hsieh et al. .................. 378/16 |
| 2004/0170254 | A1 | 9/2004 | Gregerson et al. |
| 2005/0111610 | A1 | 5/2005 | De Man et al. |
| 2006/0140340 | A1 * | 6/2006 | Kravis ......................... 378/57 |
| 2006/0193434 | A1 * | 8/2006 | Green ........................... 378/57 |

OTHER PUBLICATIONS

Jens-Peter Schlomka, Adrian Harding, Udo Van Stevendaal, Michael Grass, Geoffrey Harding; Coherent Scatter Computed Tomography—A Novel Medical Imaging Technique, Medical Imaging, Philips Research Laboratories Hamburg, Roentgenstrasse 24-26, 22335 Hamburg, Germany, 2003; Physics of Medical Imaging, Proceedings of SPIE, 2003, vol. 5030, pp. 256-265.
U.S. Appl. No. 11/434,431, filed May 15, 2006, Geoffrey Harding.
U.S. Appl. No. 11/498,114, filed Aug. 2, 2006, Geoffrey Harding.
U.S. Appl. No. 11/498,113, filed Aug. 2, 2006, Geoffrey Harding.
U.S. Appl. No. 11/484,186, filed Jul. 11, 2006, Geoffrey Harding.
U.S. Appl. No. 11/416,526, filed May 3, 2006, Geoffrey Harding et al.
U.S. Appl. No. 11/541,716, filed Sep. 29, 2006, Geoffrey Harding.
U.S. Appl. No. 11/531,019, filed Sep. 12, 2006, Geoffrey Harding.
U.S. Appl. No. 11/434,486, filed May 15, 2006, Geoffrey Harding.

(Continued)

*Primary Examiner*—Hoon Song
(74) *Attorney, Agent, or Firm*—Eugene Hyun, Esq.; Armstrong Teasdale LLP

(57) ABSTRACT

An imaging system for generating a diffraction profile is described. The imaging system includes a gantry including an x-ray imaging system configured to generate an x-ray image of a substance and a scatter system configured to generate a diffraction profile of the substance.

17 Claims, 8 Drawing Sheets

OTHER PUBLICATIONS

U.S. Appl. No. 11/434,291, filed May 15, 2006, Geoffrey Harding.
U.S. Appl. No. 11/504,395, filed Aug. 15, 2006, Geoffrey Harding.
U.S. Appl. No. 11/531,037, filed Sep. 12, 2006, Geoffrey Harding.
Hubbell, J.H., Veigele, W.J., Briggs, E.A., Brown, R.T., Cromer, D.T., Howerton, R.J., "Atomic Form Factors, Incoherent Scattering Functions and Photon Scattering Cross-sections," Journal of Physics and Chemical Reference Data, vol. 4, No. 3, pp. 471-538 (1975).
Hubbell, J.H., Veigele, W.J., Briggs, E.A., Brown, R.T., Cromer, D.T., Howerton, R.J., "Erratum; Atomic Form Factors, Incoherent Scattering Functions, and Photon Scattering Cross Sections," Journal of Physics and Chemical Reference Data, vol. 6, pp. 615-616 (1977).
Schlomka et al., "Coherent Scatter Computer Tomography—A Novel Medical Imaging Technique," Physics of Medical Imaging, Proceedings of SPIE—vol. 5030, pp. 256-265 (2003).
Rabiej M., "Determination of the Degree of Crystallinity of Semicrystalline Polymers by Means of the 'OptiFit' Computer Software," Polimery 6, pp. 423-427 (2002).
"Percentage Crystallinity Determination by X-Ray Diffraction," XRD-6000 Application Brief, Kratos Analytical—A Shimadzu Group Company, pp. 1-5 (1999).
A.M. Hindeleh and D. J. Johnson, "The Resolution of Multipeak Data in Fibre Science," J. Phys. D: Appl. Phys., vol. 4. Printed in Great Britain, pp. 259-263 (1971).

* cited by examiner

COMPACT SYSTEMS AND METHODS FOR GENERATING A DIFFRACTION PROFILE

BACKGROUND OF THE INVENTION

This invention relates generally to systems and methods for generating a diffraction profile of a substance and more particularly to providing a compact system for generating the diffraction profile.

The events of Sep. 11, 2001 instigated an urgency for more effective and stringent screening of airport baggage. The urgency for security expanded from an inspection of carry-on bags for knives and guns to a complete inspection of checked bags for a range of hazards with particular emphasis upon concealed explosives. X-ray imaging is a widespread technology currently employed for screening. However, existing x-ray baggage scanners, including computed tomography (CT) systems, designed for detection of explosive and illegal substances are unable to discriminate between harmless materials in certain ranges of density and threat materials like plastic explosive.

A plurality of identification systems based on a plurality of x-ray diffraction (XRD) techniques provide an improved discrimination of materials compared to that provided by the x-ray baggage scanners. The XRD identification systems measure a plurality of d-spacings between a plurality of lattice planes of micro-crystals in materials. However, a cost of manufacturing and implementing the XRD identification systems and the x-ray baggage scanners has increased over time.

BRIEF DESCRIPTION OF THE INVENTION

In one aspect, an imaging system for generating a diffraction profile is described. The imaging system includes a gantry including an x-ray imaging system configured to generate an x-ray image of a substance and a scatter system configured to generate a diffraction profile of the substance.

In another aspect, an imaging apparatus for generating a diffraction profile of a substance is described. The imaging apparatus includes a scatter detector and an x-ray imaging system including an x-ray source. The x-ray source is activated when a portion of the scatter detector is located at a line-of-sight passing through a centroid of the substance.

In another aspect, an imaging system for generating a diffraction profile is described. The imaging system includes a gantry including a stationary x-ray imaging system configured to generate an x-ray image of a substance and a scatter system configured to generate a diffraction profile of the substance. The imaging system further includes a processor coupled to the x-ray imaging system.

DETAILED DESCRIPTION OF THE INVENTION

Figure 1:
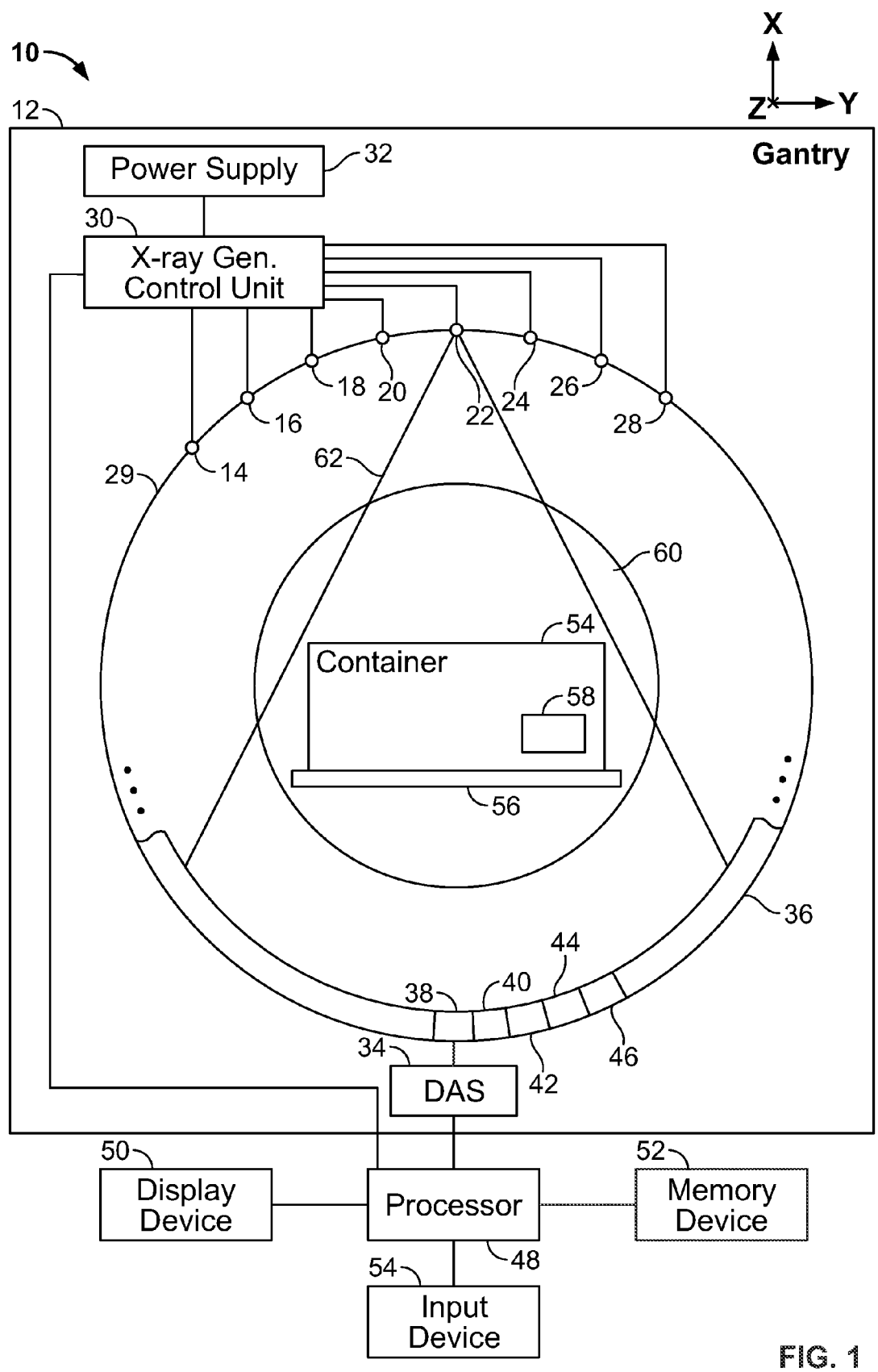
FIG. 1 is a block diagram of a system for generating an x-ray image.

FIG. 1 is a block diagram of a system 10 for generating an x-ray image. System 10 includes a stationary computed tomography (CT) system. System 10 includes a gantry 12 that includes a plurality, such as three, ten, or twenty, x-ray sources 14, 16, 18, 20, 22, 24, 26, and 28 that are stationary or cannot move. X-ray sources 14, 16, 18, 20, 22, 24, 26, and 28 are arranged circumferentially parallel to a circumference 29 of gantry 12. Gantry 12 further includes an x-ray generation control unit 30, a power supply 32, and a data acquisition system (DAS) 34. In an alternative embodiment, x-ray generation control unit 30 and power supply 32 are located outside gantry 12. Gantry 12 also includes a transmission detector 36 that is stationary or cannot move. Transmission detector 36 is located adjacent to a first xy plane that is separate from a second xy plane adjacent to x-ray sources 14, 16, 18, 20, 22, 24, 26, and 28. The first and second xy planes are part of an xyz co-ordinate system including an x-axis, a y-axis, and a z-axis. The x, y, and z axes are located within an xyz co-ordinate system. The x-axis is perpendicular to the z-axis, and the y-axis is perpendicular to the z-axis. Transmission detector 36 includes a central transmission detector element 38 or a central detector cell and a plurality of other transmission detector elements 40, 42, 44, and 46.

System 10 also includes a processor 48, a display device 50, a memory device 52, and an input device 54. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer includes a device, such as, a floppy disk drive or compact disc-read only memory (CD-ROM) drive, for reading data including the methods for generating a diffraction profile, such as a floppy disk, a CD-ROM, a magneto-optical disk (MOD), or a digital versatile disc (DVD). In another embodiment, processor 48 executes instructions stored in firmware. Examples of display device 50 include a liquid crystal display (LCD) and a cathode ray tube 1106 (CRT). Examples of input device 54 include a mouse and a keyboard. X-ray generation control unit 30 includes a pulse generator (not shown) that is coupled to processor 48 and that receives power from power supply 32. Power supply 32 is coupled to x-ray sources 14, 16, 18, 20, 22, 24, 26, and 28 to supply power to x-ray sources 14, 16, 18, 20, 22, 24, 26, and 28.

A container 54 is placed on a support 56 between x-ray sources 14, 16, 18, 20, 22, 24, 26, and 28 and transmission detector 36. Examples of container 54 include a bag, a box, and an air cargo container. Examples of each of x-ray sources 14, 16, 18, 20, 22, 24, 26, and 28 include a polychromatic x-ray source. Container 54 includes a substance 58. Examples of substance 58 include an organic explosive, an illegal drug, and a weapon, such as a gun or a knife. Examples of support 56 include a table and a conveyor belt. Container 54 is placed within an opening 60 of gantry 12 and support 56 extends along the z-axis through opening 60. Transmission detector surrounds opening 60. In an alternative embodiment, transmission detector 36 does not surround opening 60.

Processor 48 issues a command, such as a first on command, a second on command, a first off command, and a second off command. Upon receiving the first on command from processor 48, the pulse generator generates a pulse and transmits the pulse to x-ray source 22. Upon receiving a pulse from the pulse generator, x-ray source 22 generates an x-ray beam 62, such as a cone beam, under a potential applied by power supply 32. Similarly, upon receiving the first off command signal from processor 48, the pulse generator stops transmitting a pulse to x-ray source 22 and x-ray source 22 stops generating x-ray beam 62. Furthermore, upon receiving the second on command signal from processor 48, the pulse generator generates and transmits a pulse to any one of the remaining x-ray sources 14, 16, 18, 20, 24, 26, and 28 and any one of the remaining x-ray sources 14, 16, 18, 20, 24, 26, and 28 generates an x-ray beam, such as a cone beam. For example, upon receiving the second on command signal from processor 48, the pulse generator generates and transmits a pulse to x-ray source 24 and x-ray source 24 generates an x-ray beam. Upon receiving the second off command signal from processor 48, the pulse generator stops transmitting a pulse to any one of the remaining x-ray sources 14, 16, 18, 20, 24, 26, and 28 and the one of the remaining x-ray sources 14, 16, 18, 20, 24, 26, and 28 stops generating an x-ray beam. It is noted that in an alternative embodiment, system 10 includes a higher number, such as 10 or 20, or alternatively a lower number, such as 4 or 6, of x-ray sources than that shown in FIG. 1. Any of x-ray sources 14, 16, 18, 20, 22, 24, 26, and 28 are activated or turned on when the x-ray source generates an x-ray beam. On the other hand, any of x-ray sources 14, 16, 18, 20, 22, 24, 26, and 28 are deactivated or turned off when the x-ray source stops generating an x-ray beam.

X-ray source 22 generates x-ray beam 62. X-ray beam 62, which is incident on and surrounds container 54, interacts with container 54 arranged on support 56 to output x-ray radiation. Transmission detector 36 measures an intensity of the x-ray radiation and photon energy of the x-ray radiation. Transmission detector 36 measures photon energy within the x-ray radiation in an energy-sensitive manner by outputting a plurality of transmission electrical output signals dependent on a plurality of energies of x-ray quanta detected from within the x-ray radiation. Central transmission detector element 38 is located at a center of an arc of transmission detector 36 and the x-ray radiation is incident on the arc.

DAS 34 samples analog data, such as transmission electrical output signals, generated from transmission detector elements 38, 40, 42, 44, and 46 of transmission detector 36 and converts the analog data to a plurality of digital signals for subsequent processing. Processor 48 receives sampled and digitized x-ray data from DAS 34, performs pre-processing, such as filtering or amplifying, on the sampled and digitized x-ray data to generate pre-processed data, and performs image reconstruction on the pre-processed data to generate an x-ray image, such as a CT image. The x-ray image may be a two-dimensional (2D) or alternatively a three-dimensional (3D) image. Examples of the image reconstruction include filtered backprojection (FBP) and iterative reconstruction (IR). The image reconstruction converts a plurality of attenuation measurements from a scan conducted by system 10 into integers called CT numbers, measured in Hounsfield units (HUs), which are used to control a brightness of a corresponding pixel on display device 50. Processor 48 displays the x-ray image on display device 50 and stores the x-ray image in memory device 52.

Figure 2:
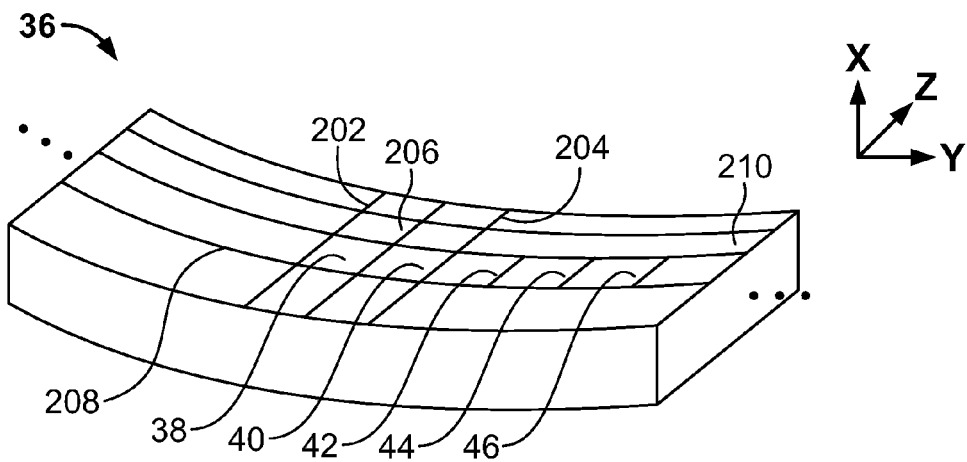
FIG. 2 is an isometric view of an embodiment of a transmission detector of the system of FIG. 1.

FIG. 2 is an isometric view of an embodiment of transmission detector 36. Transmission detector 36 includes a plurality of rows 202 and 204 of transmission detector elements 38, 40, and a transmission detector element 206, and rows 202 and 204 are parallel to the z-axis. For example, row 202 includes central transmission detector element 38 and transmission detector element 206. Transmission detector 36 further includes a plurality of columns 208 and 210 of transmission detector elements 38, 40, 42, 44, 46, and 206, and the columns 208 and 210 are perpendicular to rows 202 and 204. For example, column 208 includes transmission detector elements 38, 40, 42, 44, and 46. In an alternative embodiment, transmission detector 36 includes one column of transmission detector elements.

Figure 3:
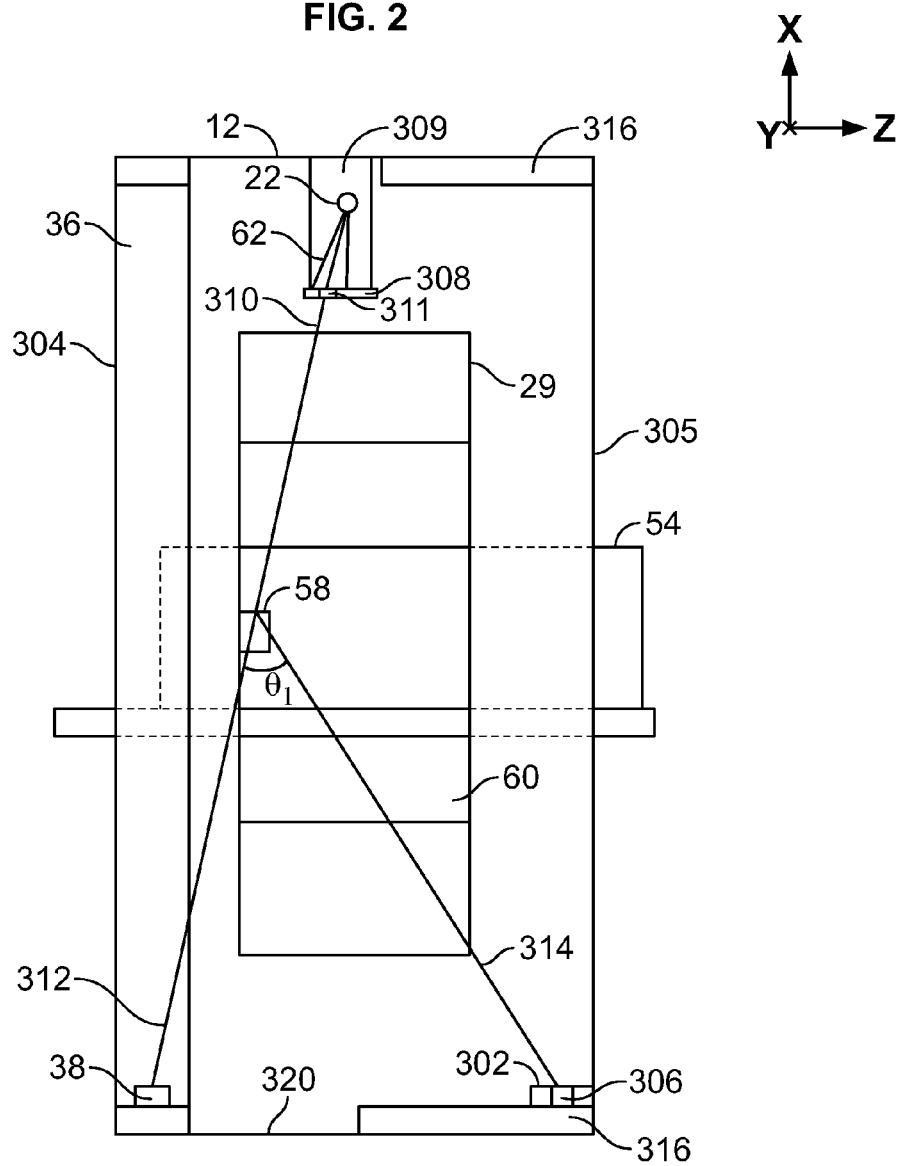
FIG. 3 is a side view of an embodiment of a gantry located within the system of FIG. 1.

FIG. 3 is a side view of an embodiment of gantry 12. Gantry 12 includes opening 60, transmission detector 36, a scatter detector 302, and a primary collimator 308. Primary collimator 308 is attached, such as bolted, to a portion 309 or an extension of gantry 12. Portion 309 includes an aperture (not shown) for passage of x-ray beam 62. An example of primary collimator 308 includes a plate or a sheet. An example of scatter detector 302 includes a detector fabricated from Germanium or Cadmium Zinc Telluride (CdZnTd). Transmission detector 36 is circumferentially located adjacent to the first xy plane and parallel to circumference 29 of gantry 12. Transmission detector 36 is adjacent to a side 304 of gantry 12. Scatter detector 302 is located parallel to circumference 29 of gantry 12. Scatter detector 302 is located adjacent to a side 305 of gantry 12. Side 304 is located in a first z-direction opposite to a second z-direction in which side 305 of gantry 12 is located. The first and second z-directions are parallel to the z-axis. In an alternative embodiment, scatter detector 302 does not surround opening 60. Scatter detector 302 includes a plurality of scatter detector elements including a scatter detector element 306. Scatter detector 302 is located adjacent to a third xy plane that is parallel to the first and second xy planes and separate from the first and second xy planes.

X-ray source 22 generates x-ray beam 62 that passes through the aperture of portion 309. Primary collimator 308 collimates x-ray beam 62 to generate a collimated beam 310, such as a fan beam. Container 54 receives collimated beam 310 that passes through an aperture 311 of primary collimator 308. When collimated beam 310 reaches substance 58, substance 58 interacts with collimated beam 310 to output a primary x-ray beam 312 and a scattered x-ray beam 314. Any scattered x-ray beam generated upon a collimated beam being incident on substance 58 includes coherent scatter. Scatter detector 302 detects scattered x-ray beam 314 to generate a plurality of scattered electrical output signals. A constant scatter angle $\theta_1$ is formed between primary x-ray beam 312 and scattered x-ray beam 314. Moreover, scatter angles, other than scatter angle $\theta_1$, are formed between primary x-ray beam 312 and scattered x-ray beams, other than scattered x-ray beam 314, generated when collimated beam 310 passes through substance 58. Gantry 12 further includes a guide rail 316 that supports scatter detector 302. Guide rail 316 is attached, such as glued or bolted, to a surface 320 inside gantry 12. Guide rail 316 is located circumferentially surrounding opening 60 and is parallel to circumference 29 of gantry 12. For example, guide rail 316 extends along and is adjacent to the third xy plane.

Figure 4:
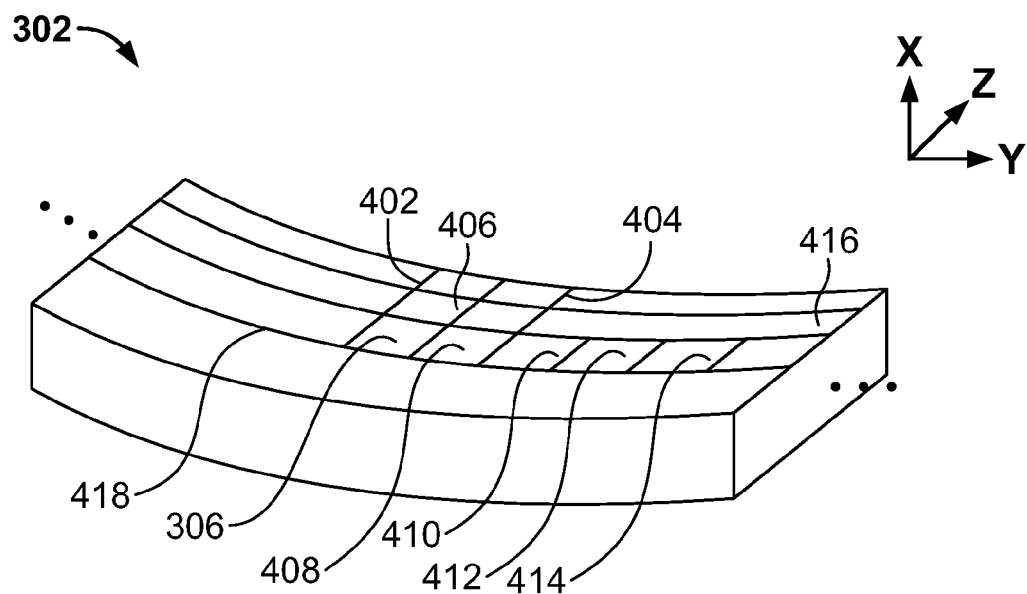
FIG. 4 is an isometric view of an embodiment of a scatter detector located within the system of FIG. 1.

FIG. 4 is an isometric view of an embodiment of scatter detector 302. Scatter detector 302 includes a plurality of rows 402 and 404 of scatter detector elements 306, 406, and 408, and rows 402 and 404 are parallel to the z-axis. For example, row 402 includes scatter detector element 306 and scatter detector element 406. Scatter detector 302 further includes a plurality of columns 416 and 418 of scatter detector elements 306, 406, 408, 410, 412, and 414 and the columns 416 and 418 are perpendicular to rows 402 and 404. For example, column 418 includes scatter detector elements 306, 408, 410, 412, and 414. In an alternative embodiment, scatter detector 302 includes one column of scatter detector element.

Figure 5:
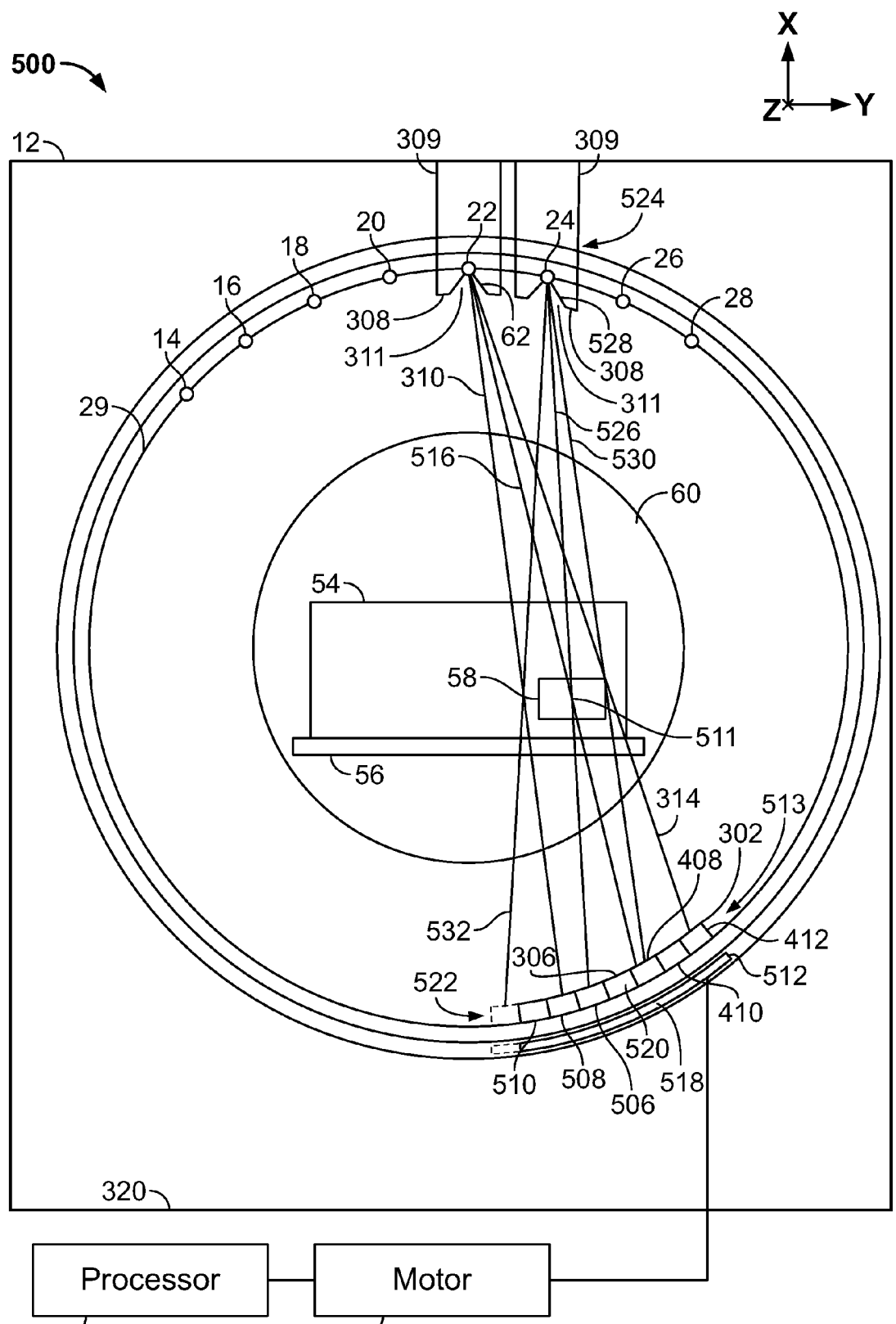
FIG. 5 is a block diagram of an embodiment of a system for generating a diffraction profile.

FIG. 5 is a block diagram of an embodiment of a system 500 for generating a diffraction profile. System 500 is an example of system 10 (FIG. 1). System 500 includes gantry 12, scatter detector 302, and guide rail 316. System 500 includes a plurality of portions 309, and a plurality of primary collimators 308. Each primary collimator 308 has aperture 311 and is attached, such as bolted, to respective portions 309 of gantry 12. Each primary collimator 308 is stationary. System 500 further includes processor 48 and a motor 502. Scatter detector 302 includes scatter detector elements 306, 408, 410, 412, and a plurality of scatter detector elements 506, 508, and 510. Processor 48 segments the x-ray image to distinguish an image of substance 58 from the remaining of the x-ray image. Processor 48 segments the x-ray image based on a CT number. Upon determining by processor 48 that a CT number of a portion of the x-ray image lies within a range from and including A HUs to B HUs, processor 48 determines that the portion is a portion of an image of substance 58. On the other hand, upon determining by processor 48 that a CT number of a portion of the x-ray image lies outside the range from and including A HUs to B HUs, processor 48 determines that the portion is a portion of the remaining of the x-ray image. Processor 48 segments the x-ray image to generate a segmented substance image, such as a two-dimensional (2D) or a three-dimensional (3D) image, of substance 58. Processor 48 determines a centroid 511 of the segmented substance image within the xyz co-ordinate system. Centroid 511 is the centroid 511 of substance 58 when the segmented substance image has the same dimensions as substance 58 and the x-ray image is generated with respect to the xyz co-ordinate system.

Processor 48 sends a first position control signal to motor 502. Upon receiving the first position control signal, motor 502 slides a carriage 512 attached to scatter detector 302 to a first position 513 to move scatter detector 302 to the first position 513. When carriage 512 is located at the first position 513, x-ray source 22 is located at a point on a line-of-sight 516 joining x-ray source 22, centroid 511 of substance 58, and a center 518 of carriage 512. Scatter detector 302 is placed symmetrically with respect to and attached to carriage 512 so that center 518 of carriage 512 coincides with a center 520, located at a point on line-of-sight 516, of scatter detector 302.

When carriage 512 is at the first position 513, processor 48 activates x-ray source 22 for a time $t_1$ to generate x-ray beam 62. An example of $t_1$ includes an amount of time in which a shadow of substance 58 travels a distance of one tenth of a width, parallel to circumference 29 of gantry 12, of scatter detector element 306. Another example of $t_1$ includes $$t_1 = \frac{m(\text{pitch})(D_1)}{R\omega D_2} \quad (1)$$

where m ranges from and including 0.1 to 0.5, R is a radius of guide rail 316, which is circular, ω is an angular velocity of carriage 512 in moving to the first position 513 along guide rail 316, pitch is a distance between center 520 of scatter detector element 306 and scatter detector element 408 adjacent to scatter detector element 306, $D_1$ is a distance between scatter detector element 306 located at a center of scatter detector 302 and centroid 511 when carriage 512 is at the first position 513, and $D_2$ is a distance between centroid 511 and x-ray source 22 that is activated when carriage 512 is at the first position 513. As an example, the radius R is equal to a radius of transmission detector 36. As another example, the radius R is different than a radius of transmission detector 36. A user, such as a person, inputs a plurality of positions, within the xyz co-ordinate system, of x-ray sources 14, 16, 18, 20, 22, 24, 26, and 28 to processor 48 via input device 54. The positions include a position $p_1$ of x-ray source 22 and a position $p_2$ of x-ray source 24. Processor 48 determines a position $r_1$ of scatter detector element 306 within the xyz co-ordinate system as a position of a point at an intersection of line-of-sight 516 passing through centroid 511 with scatter detector element 306. Processor 48 determines $D_1$ as a distance between the position $r_1$ and centroid 511. Processor 48 determines $D_2$ as a distance between the position $p_1$ and centroid 511.

Primary collimator 308 collimates x-ray beam 62 generated for time $t_1$ to generate collimated beam 310 from aperture 311 of primary collimator 308. Based on a size of the segmented substance image, the user designs and fabricates primary collimator 308 having aperture 311 that outputs collimated beam 310 surrounding substance 58. Collimated beam 310 has a smaller size than x-ray beam 62. For example, a portion of collimated beam 310 incident on transmission detector 36 has a smaller arc length than an arc length, if incident on transmission detector 36, of x-ray beam 62. Collimated beam 310 passes through substance 58 and substance 58 interacts with collimated beam 310 to output primary x-ray beam 312 that is detected by transmission detector 36 and to output scattered x-ray beam 314 that is detected by scatter detector 302. Transmission detector 36 detects primary x-ray beam 312 to generate a plurality of transmission electrical output signals. Processor 48 deactivates x-ray source 22 after time $t_1$.

Processor 48 sends a second position control signal to motor 502. Upon receiving the second position control signal, motor 502 slides carriage 512 from the first position 513 to a second position 522 to move scatter detector 302 to the second position 522. When carriage 512 is located at the second position 522, x-ray source 24 is located at a point on a line-of-sight 526 joining x-ray source 24, centroid 511 of substance 58, and center 518 of carriage 512. Scatter detector 302 is placed symmetrically with respect to and attached to carriage 512 so that center 518 of carriage 512 coincides with center 520, located at a point on line-of-sight 526, of scatter detector 302.

When carriage 512 is at the second position 522, processor 48 activates x-ray source 24 for a time $t_2$ to generate an x-ray beam 528. X-ray sources 22 and 24 are activated sequentially by processor 48. An example of $t_2$ includes an amount of time in which a shadow of substance 58 travels a distance of one tenth of a width, parallel to circumference 29 of gantry 12, of scatter detector element 306. Another example of $t_2$ includes $$t_2 = \frac{m(\text{pitch})(D_3)}{R\omega D_4} \quad (2)$$

where ω is an angular velocity of carriage 512 in moving from the first position 513 to the second position 522 along guide rail 316, $D_3$ is a distance between scatter detector element 306 and centroid 511 when carriage 512 is at the second position 522, and $D_4$ is a distance between centroid 511 and x-ray source 24 that is activated when carriage 512 is at the second position 522. An example of the angular velocity ω includes an angular velocity having a frequency ranging from and including 0.9 hertz (Hz) to 1.1 Hz. Processor 48 determines a position $r_2$ of scatter detector element 306 within the xyz co-ordinate system as a position of a point at an intersection of line-of-sight 526 passing through centroid 511 with scatter detector element 306. Processor 48 determines $D_3$ as a distance between the position $r_2$ and centroid 511. Processor 48 determines $D_4$ as a distance between the position $p_2$ and centroid 511.

Primary collimator 308 collimates x-ray beam 528 generated for time $t_2$ to generate a collimated beam 530 from aperture 311 of primary collimator 308. Collimated beam 530 has a smaller size than x-ray beam 528. For example, a portion of collimated beam 530 incident on transmission detector 36 is has a smaller arc length than an arc length, if incident on transmission detector 36, of x-ray beam 528. Collimated beam 530 passes through substance 58 and substance 58 interacts with collimated beam 530 to output a primary x-ray beam (not shown) that is detected by transmission detector 36 and to output a scattered x-ray beam 532 that is detected by scatter detector 302. Processor 48 deactivates x-ray source 24 after time $t_2$.

Similarly, processor 48 moves scatter detector 302 along guide rail 316 located parallel to circumference 29 of gantry 12 in either a clockwise direction or a counterclockwise direction and sequentially activates the remaining x-ray sources, such as x-ray sources 26, 28, 14, 18, and 20, of system 10. Respective primary collimators 308 collimate an x-ray beam generated by respective remaining x-ray sources, including x-ray sources 26, 28, 14, 16, 18, and 20, within gantry 12 to generated a collimated beam. Processor 48 continuously moves scatter detector 302 along guide rail 316 at the angular velocity ω. For example, processor 48 circumferentially moves scatter detector 302 for 180 degrees and the movement is parallel to circumference 29 of gantry 12 to generate a diffraction profile of substance 58. As another example, processor 48 circumferentially moves scatter detector 302 for 360 degrees parallel to circumference 29 of gantry 12 to generate a diffraction profile of substance 58.

Figure 6:
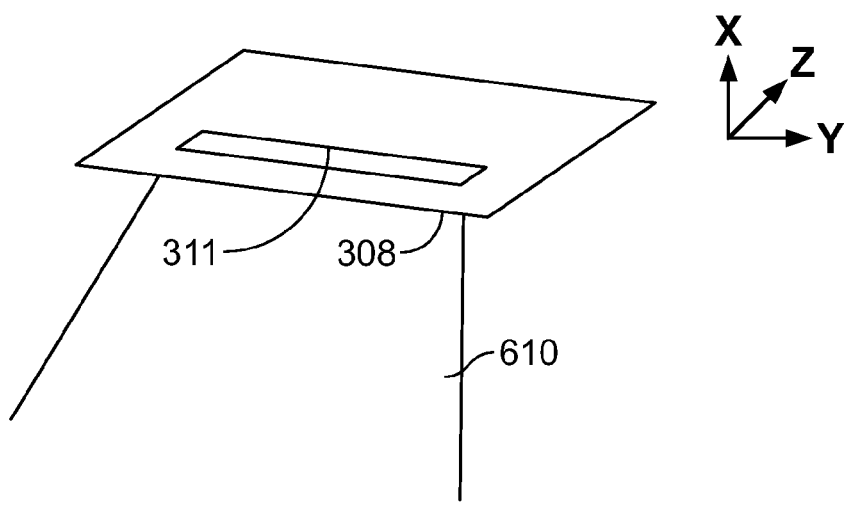
FIG. 6 is an isometric view of an embodiment of a primary collimator located within the system of FIG. 5.

FIG. 6 is an isometric view of an embodiment of primary collimator 308. Primary collimator 308 includes aperture 311. Primary collimator 308 collimates an x-ray beam to generate a collimated beam 610, such as a fan beam, that passes through aperture 311. Collimated beam 610 is an example of each of collimated beams 310 and 530. Primary collimator 308 is fabricated from a material, such as tungsten or molybdenum.

Figure 7:
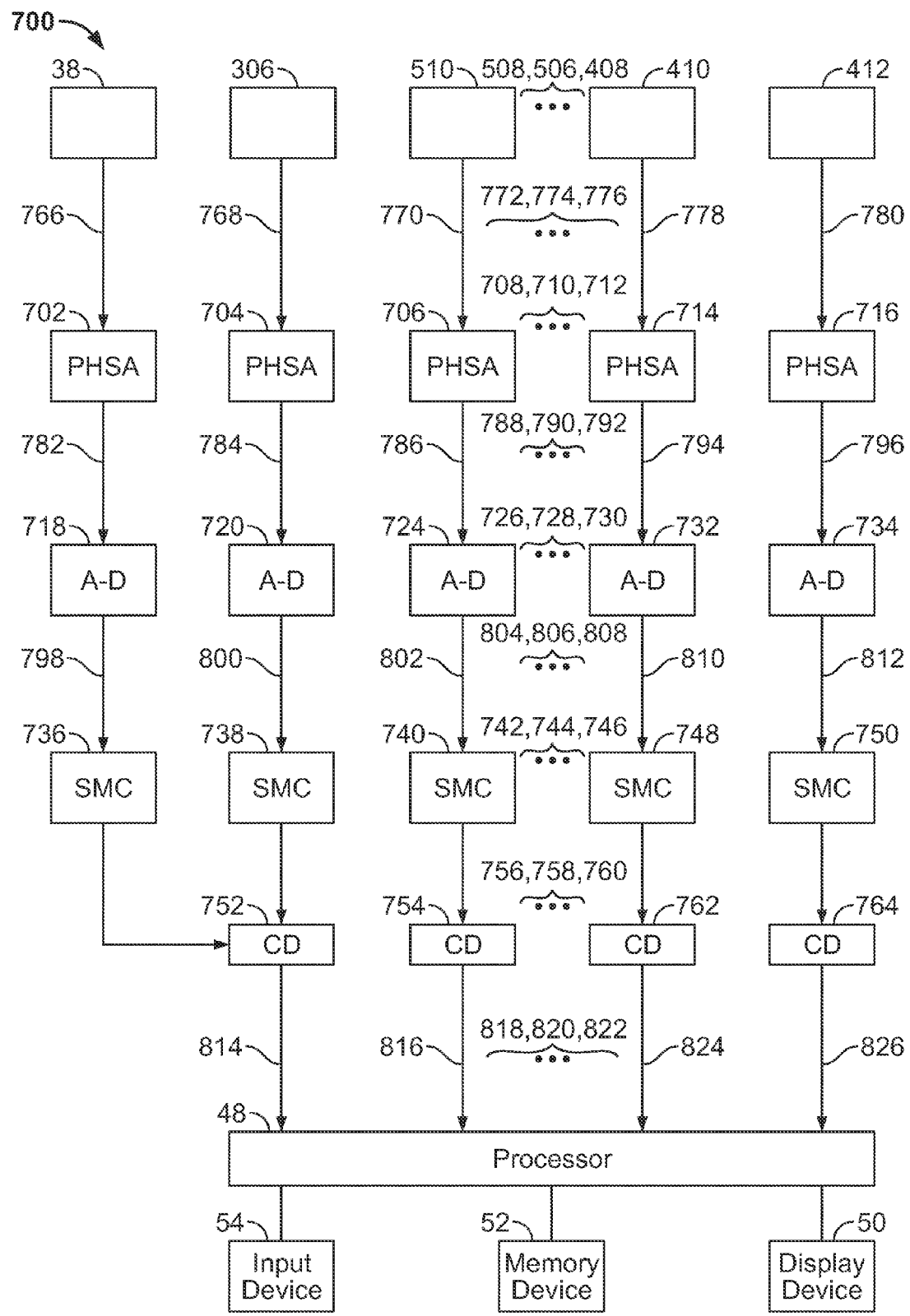
FIG. 7 is a block diagram of an embodiment of a system for generating a diffraction profile of a substance.

FIG. 7 is a block diagram of an embodiment of a system 700 for generating a diffraction profile of a substance 58. System 700 includes central transmission detector element 38, scatter detector elements 306, 510, 508, 506, 408, 410, and 412, a plurality of pulse-height shaper amplifiers (PHSA) 702, 704, 706, 708, 710, 712, 714, and 716, a plurality of analog-to-digital (A-to-D) converters 718, 720, 722, 724, 726, 728, 730, 732, and 734, a plurality of spectrum memory circuits (SMCs) 736, 738, 740, 742, 744, 746, 748, and 750 allowing pulse height spectra to be acquired, a plurality of correction devices (CDs) 752, 754, 756, 758, 760, 762, and 764, processor 48, input device 54, display device 50, and memory device 52. An example of each of correction devices 752, 754, 756, 758, 760, 762, and 764 include a divider circuit. Each of spectrum memory circuits 736, 738, 740, 742, 744, 746, 748, and 750 include an adder and a memory device, such as a random access memory (RAM) or a ROM.

Central transmission detector element 38 is coupled to pulse-height shaper amplifier 702, and scatter detector elements 306, 510, 508, 506, 408, 410, and 412 are coupled to pulse-height shaper amplifiers 704, 706, 708, 710, 712, 714, and 716, respectively. Central transmission detector element 38 generates a transmission electrical output signal 766 by detecting a portion of a plurality of primary x-ray beams, such as primary x-ray beam 312 and the primary x-ray beam generated by activating x-ray source 24, and scatter detector elements 306, 510, 508, 506, 408, 410, and 412 generate a plurality of scatter electrical output signals 768, 770, 772, 774, 776, 776, and 780 by detecting a plurality of scattered x-ray beams, such as scattered x-ray beam 314 and scattered x-ray beam 532. For example, scatter detector element 306 generates scatter electrical output signal 768 for each scattered x-ray photon incident on scatter detector element 306. Each pulse-height shaper amplifier amplifies an electrical output signal received from a detector element. For example, pulse-height shaper amplifier 702 amplifies transmission electrical output signal 766 and pulse-height shaper amplifier 704 amplifies scatter electrical output signal 768. Pulse-height shaper amplifiers 702, 704, 706, 708, 710, 712, 714, and 716 have a gain factor determined by processor 48 or alternatively input to processor 48 via input device 54 by the user.

An amplitude of an electrical output signal from a detector element is proportional to an energy of an x-ray quantum that is detected by the detector element to generate the electrical output signal. For example, an amplitude of transmission electrical output signal 766 is proportional to an energy of an x-ray quantum in primary x-ray beam 312 detected by central transmission detector element 38. On the other hand, an amplitude of scatter electrical output signal 768 is proportional to an energy of an x-ray quantum within scattered x-ray beam 314 that is detected by scatter detector element 306.

A pulse-height shaper amplifier generates an amplified output signal by amplifying an electrical output signal generated from a detector element. For example, pulse-height shaper amplifier 702 generates an amplified output signal 782 by amplifying transmission electrical output signal 766 and pulse-height shaper amplifier 104 generates an amplified output signal 784 by amplifying scatter electrical output signal 768. Similarly, a plurality of amplified output signals 786, 788, 790, 792, 794, and 796 are generated. An analog-to-digital converter converts an amplified output signal from an analog form to a digital form to generate a digital output signal. For example, analog-to-digital converter 718 converts amplified output signal 782 from an analog form to a digital format to generate a digital output signal 798. Similarly, a plurality of digital output signals 800, 802, 804, 806, 808, 810, and 812 are generated by analog-to-digital converters 720, 722, 724, 726, 728, 730, 732, and 734, respectively. A digital value of a digital output signal generated by an analog-to-digital converter represents an amplitude of energy or alternatively an amplitude of intensity of a pulse of an amplified output signal. Each pulse is generated by an x-ray quantum, such as an x-ray photon. For example, a digital value of digital output signal 798 output by analog-to-digital converter 718 is a value of an amplitude of a pulse of amplified output signal 782.

An adder of a spectrum memory circuit adds a number of pulses in a digital output signal. For example, when analog-to-digital converter 718 converts a pulse of amplified output signal 782 into digital output signal 798 to determine an amplitude of the pulse of amplified output signal 782, an adder within spectrum memory circuit 736 increments, by one, a value within a memory device 52 of spectrum memory circuit 736. Accordingly, at an end of an x-ray examination of substance 58, a memory device within a spectrum memory circuit stores a number of x-ray quanta detected by a detector element. For example, a memory device within spectrum memory circuit 736 stores a number of x-ray photons detected by transmission detector element 38 and each of the x-ray photons has an amplitude of energy or alternatively an amplitude of intensity that is determined by analog-to-digital converter 718.

A correction device receives a number of x-ray quanta that have a range of energies and are stored within a memory device of one of spectrum memory circuits 738, 740, 742, 744, 746, 748, and 750, and divides the number by a number of x-ray quanta having the range of energies received from a memory device of spectrum memory circuit 736. For example, correction device 752 receives a number of x-ray photons having a range of energies from a memory device of spectrum memory circuit 738, and divides the number by a number of x-ray photons having the range received from a memory device of spectrum memory circuit 736. Each correction device outputs a correction output signal that represents a range of energies within x-ray quanta received by a detector element. For example, correction device 752 outputs a correction output signal 814 representing an energy spectrum or alternatively an intensity spectrum within x-ray quanta detected by scatter detector element 306. As another example, correction device 754 outputs a correction output signal 816 representing an energy spectrum within x-ray quanta detected by scatter detector element 510. Similarly, a plurality of correction output signals 818, 820, 822, 824, and 826 are generated by correction devices, respectively.

Processor 48 receives correction output signals 814, 816, 818, 820, 822, 824, and 826 to generate a momentum transfer x, measured in inverse nanometers ($nm^{-1}$), from an energy spectrum r(E) of energy E of x-ray quanta within scattered x-ray beams detected by scatter detector 302. Processor 48 generates the momentum transfer x by applying $$x=(E/hc)\sin(\theta/2) \quad (3)$$

where c is a speed of light, h is Planck's constant, θ represents a constant scatter angle, such as the scatter angle $\theta_1$, of x-ray quanta of a scattered x-ray beam detected by the scatter detector 302. Processor 48 relates the energy E to the momentum transfer x by equation (3). Processor 48 190 receives the scatter angle θ from the user via input device 54. Processor 48 generates a diffraction profile of substance 58 by calculating a number of x-ray photons that are detected by scatter detector 302 and by plotting the number versus the momentum transfer x. There is no unique or one-to-one relationship between an origin of a scattered beam and a scatter detector element, of scatter detector 302, that detects the scattered beam. Accordingly, the diffraction profile of substance 58 is reconstructed by processor 48. An example of the reconstruction of a diffraction profile is provided in Schlomka et al., Coherent Scatter Computed Tomography—A Novel Medical Imaging Technique, Proceedings of SPIE—Volume 5030 (2003), pages 256-265.

It is noted that a number of pulse-height shaper amplifiers 702, 704, 706, 708, 710, 712, 714, and 716 changes with a number of detector elements 38, 306, 510, 508, 506, 408, 410, and 412. For example, five pulse-height shaper amplifiers are used for amplifying signals received from five detector elements. As another example, four pulse-height shaper amplifiers are used for amplifying signals received from four detector elements. Similarly, a number of analog-to-digital converters 718, 720, 722, 724, 726, 728, 730, 732, and 734 changes with a number of detector elements 38, 306, 510, 508, 506, 408, 410, and 412 and a number of spectrum memory circuits 736, 738, 740, 742, 744, 746, 748, and 750 changes with the number of detector elements 38, 306, 510, 508, 506, 408, 410, and 412.

Figure 8:
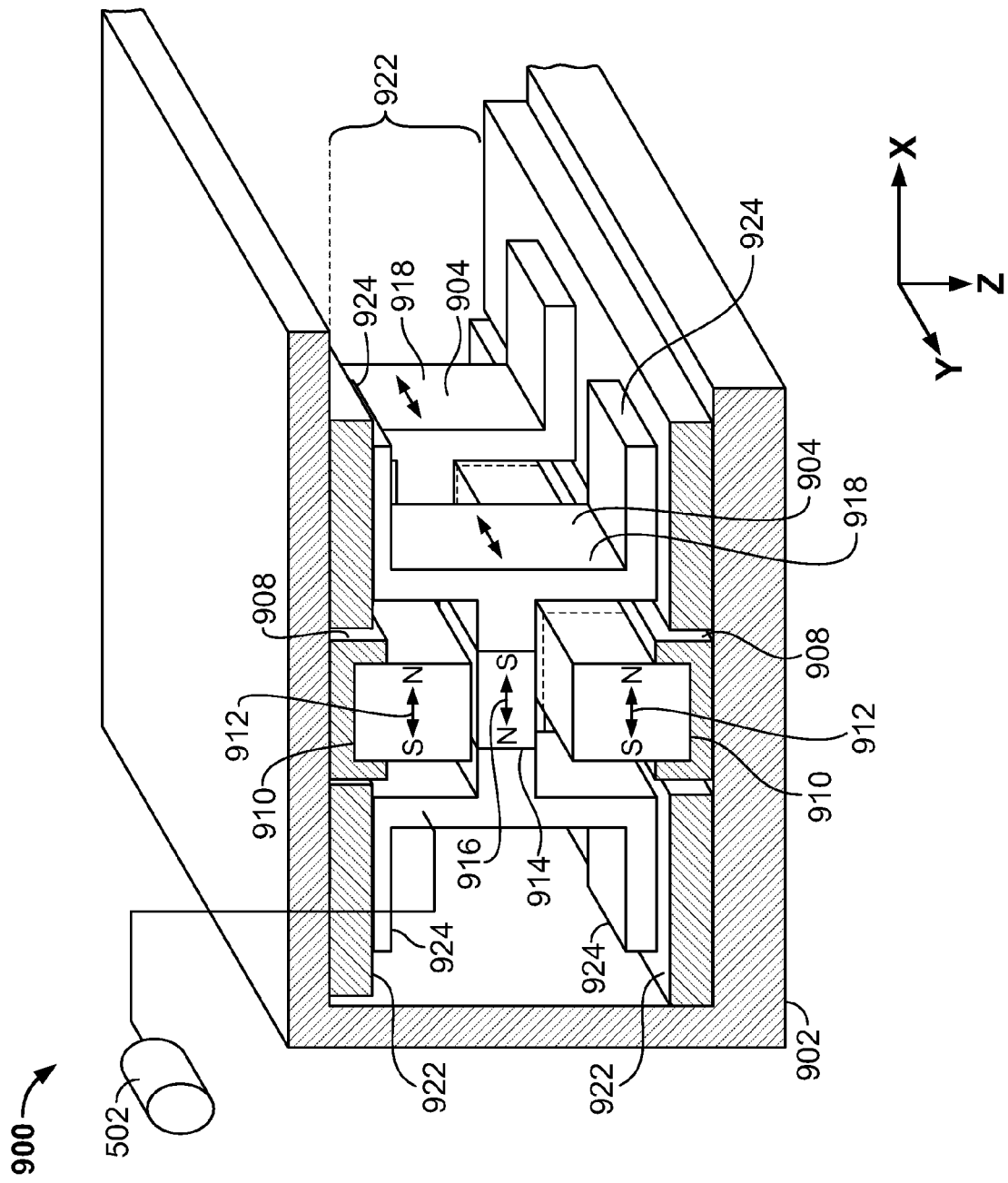
FIG. 8 is an isometric view of an embodiment of a transport apparatus located within the system of FIG. 5.

FIG. 8 is an isometric view of an embodiment of a transport apparatus 900 that includes a guide rail 902, at least one carriage 904, and motor 502 for propelling carriage 904 along guide rail 316. Guide rail 902 and carriage 904 are fabricated from a metal, such as aluminum or steel. Guide rail 902 is an example of guide rail 316. Carriage 904 is an example of carriage 512. Guide rail 902 includes one or alternatively more track elements 908, made of the metal, and a plurality of track magnets 910 having a magnetization vector indicated by an arrow 912. Each carriage 904 includes one or alternatively more carriage magnets 914 having a magnetization vector indicated by an arrow 916. Track magnets 910 and carriage magnets 914 interact to magnetically support each carriage 904 on guide rail 902 in a first direction, such as a clockwise direction or a counterclockwise direction. A passive stabilization support 922, made of the metal, supports each carriage 904 in a second direction, which is a direction parallel to the z-axis and orthogonal to the first direction.

Transport apparatus 900 is implemented within gantry 12 by attaching guide rail 902 to surface 320 inside gantry 12. Moreover, scatter detector 302 is attached, such as glued, bolted, or soldered, to a surface 918 of carriage 904. For example, a position of carriage 904 is within a range from and including 24 micrometers to 26 micrometers with respect to a position of scatter detector 302. Accordingly, when carriage 904 moves along guide rail 902, scatter detector 302 moves along guide rail 902. Track magnets 910 and carriage magnets 914 interact to magnetically support carriage 904 in guide rail 902 in the first direction, while passive stabilization support 922 stabilizes a plurality of positions of carriage 904 in the second direction by constraining the motion of carriage 904 to an xy-plane formed by the x and y axes. Passive stabilization support 922 is air bearing and is coupled without friction to at least one floatation pad 924, made of a plastic, on carriage 904.

Figure 9:
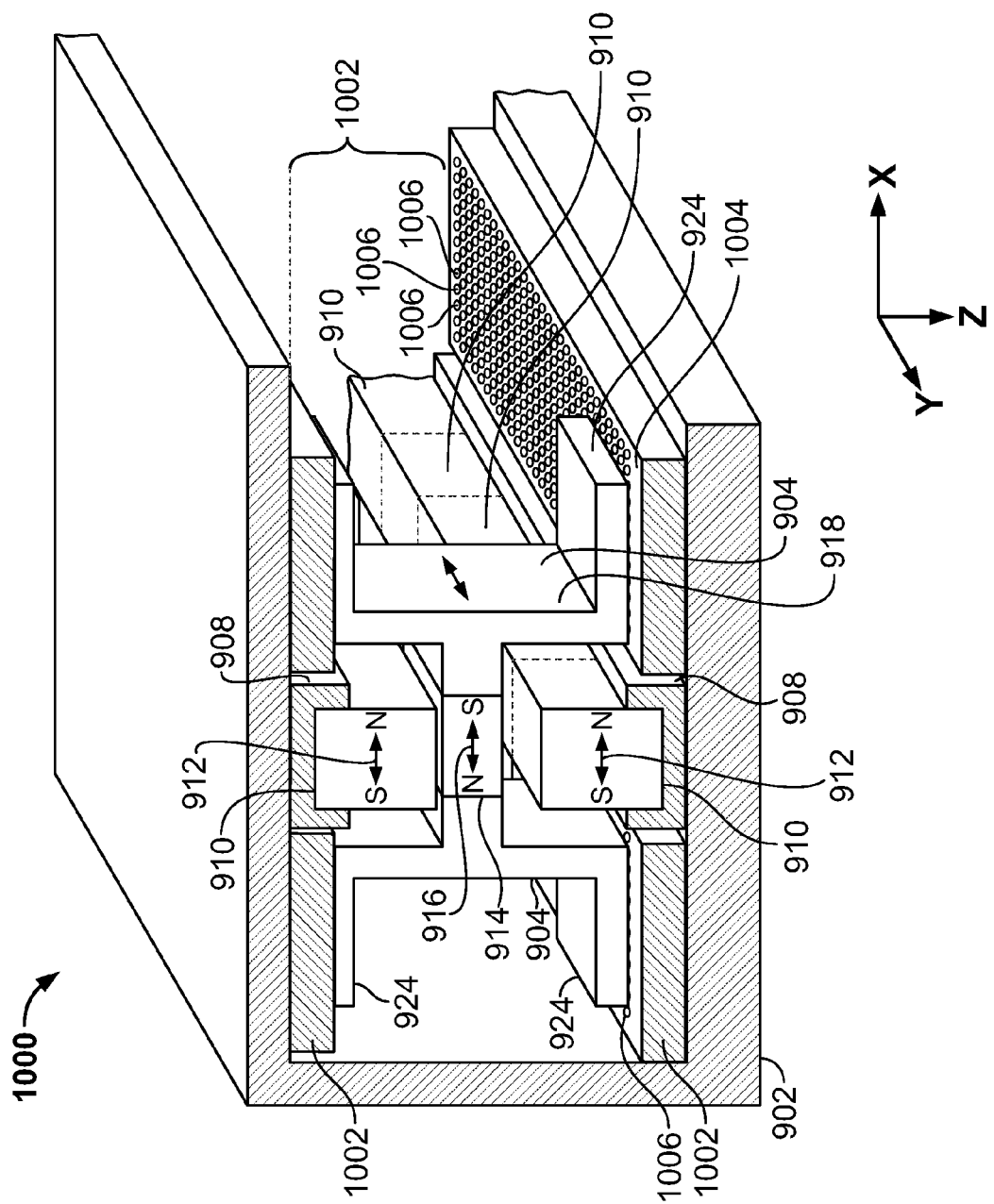
FIG. 9 is an isometric view of another embodiment of a transport apparatus located within the system of FIG. 5.
Figure 10:
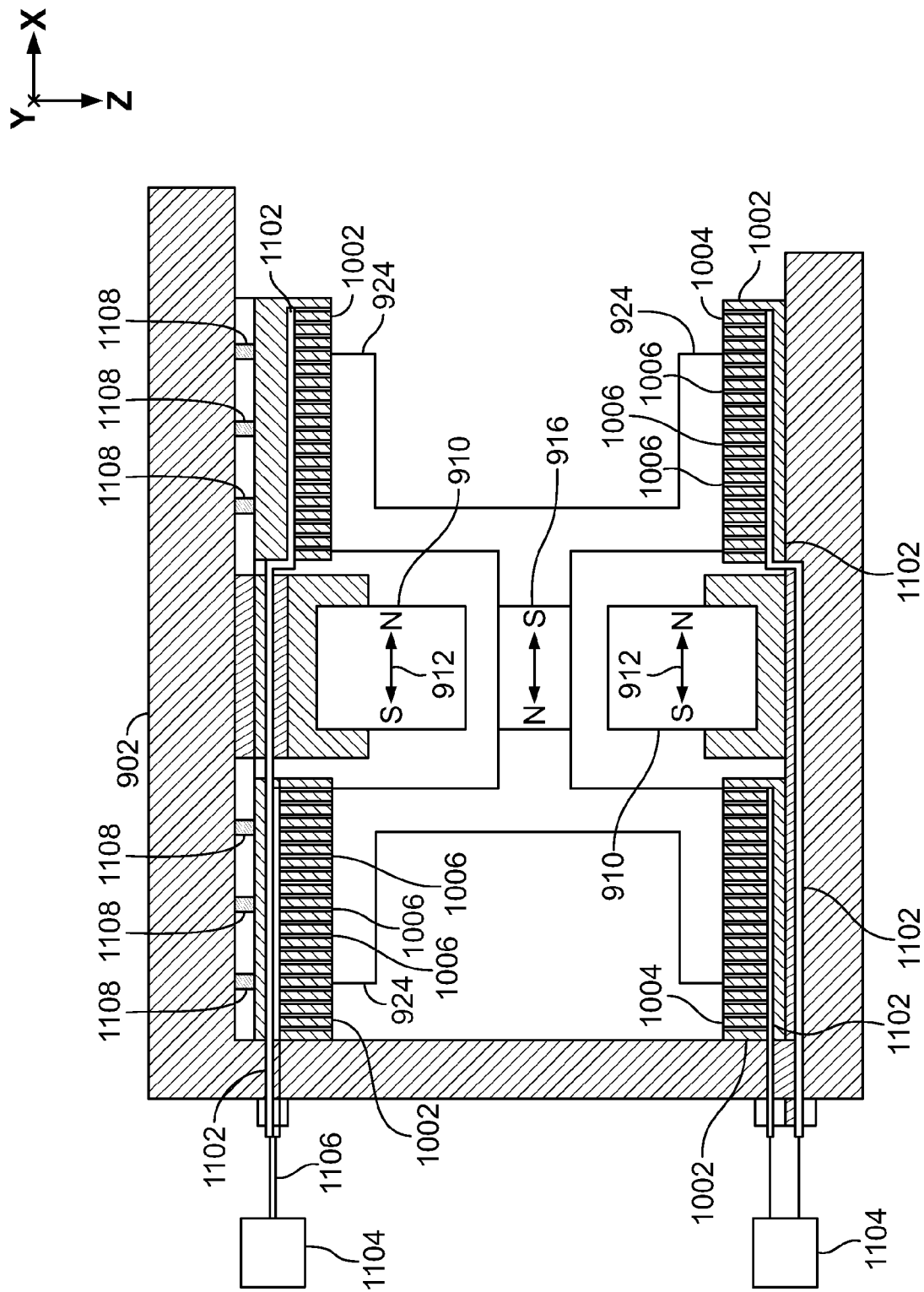
FIG. 10 shows a view of the transport apparatus of FIG. 9.

FIG. 9 is an isometric view of an embodiment of a transport apparatus 1000, which is an example of transport apparatus 900. A slideway 1002, which is an example of passive stabilization support 922, is mounted to guide rail 902. Slideway 1002 includes at least one planar gas-permeable bearing surface 1004 or at least one bearing platen, and includes a gas distribution apparatus 1102 (shown in FIG. 10). Gas-permeable bearing surface 1004 may either be porous or have a plurality of orifices 1006 thereon FIG. 10 shows a view of transport apparatus 900. A pressurized gas supply 1104 is connected to gas distribution apparatus 1102 by a tube 1106. Gas distribution apparatus 1102 may either be a manifold or may be a permeable substrate within slideway 1002. Pressurized gas supply 1104 provides a sufficient flow of gas through tube 1106 and the gas distribution apparatus 1102 and then through orifices 1006 in gas-permeable bearing surface 1004 to support pad 924 on a thin layer of gas.

The plane of gas-permeable bearing surfaces 1004 is parallel to the xy-plane, which is perpendicular to the z-axis. At least one pad 924 is mounted on carriage 904 such that the plane of each pad 924 is oriented along a plane parallel to the orientation of the corresponding gas-permeable bearing surface 1004, so that each pad 924 on carriage 904 is supported by the corresponding gas-permeable bearing surface 1004 in a non-contacting, friction-free manner. Track magnets 910 are each displaced in the first direction in a symmetrical manner have magnetization vectors. An arrangement of a plurality of springs 1108 allows gas-permeable bearing surfaces 1004 some vertical movement to accommodate minor alignment irregularities of guide rail 902. Springs 1108 both preload gas-permeable bearing surface 1004 and permit a gap between pads 924 on carriage 904 and gas-permeable bearing surfaces 1004 on guide rail 902 to remain relatively constant without undue manufacturing precision of guide rail 902.

Technical effects of the herein described systems and methods for generating a diffraction profile include providing a compact system including transmission detector 36, scatter detector 302, and x-ray sources 14, 16, 18, 20, 22, 24, 26, and 28 within the same gantry 12. Other technical effects include using the same x-ray sources 14, 16, 18, 20, 22, 24, 26, and 28 to generate the x-ray image and a diffraction profile of substance 58. X-ray sources 14, 16, 18, 20, 22, 24, 26, and 28 are activated to generate x-ray beams with portions that pass through substance 58. Transmission detector 36 measures an intensity of x-ray radiation that is output from substance 58 to generate a plurality of transmission electrical output signals. Processor 48 generates the x-ray image of substance 58 from the transmission electrical output signals and segments the x-ray image to output the segmented substance image.

Moreover, each x-ray source 14, 16, 18, 20, 22, 24, 26, and 28 is activated for a time, such as the time $t_1$ or $t_2$, to generate an x-ray beam that is collimated to output a collimated beam. A collimated beam passes through centroid 511 represented within the segmented substance image to output scattered x-ray beams that are detected by scatter detector 302. Scatter detector 302 generates a plurality of scatter electrical output signals from scattered x-ray beams and processor 48 generates the diffraction profile from the scatter electrical output signals. Hence, the same x-ray sources 14, 16, 18, 20, 22, 24, 26, and 28 are used to generate the x-ray image and a diffraction profile of substance 58. Yet other technical effects include the provision of the compact system and use of the same x-ray sources 14, 16, 18, 20, 22, 24, 26, and 28. The provision of the compact system and use of the same x-ray sources 14, 16, 18, 20, 22, 24, 26, and 28 results in a lower cost than a cost for fabricating a system within separate x-ray imaging and x-ray diffraction systems. Still other technical effects include using the diffraction profile to confirm an identity of substance 58 with respect to an identity of substance 58 determined from the x-ray image. For example, processor 58 generates an effective atomic number and a packing fraction of substance 58 to confirm an identify of substance 58 determined from CT numbers within the x-ray image.

While the invention has been described in terms of various specific embodiments, those skilled in the art will recognize that the invention can be practiced with modification within the spirit and scope of the claims.

What is claimed is:

1. An imaging system for generating a diffraction profile of a substance, said imaging system comprising:
   a plurality of stationary radiation sources;
   a transmission detector configured to receive a primary beam generated by at least one stationary radiation source of said plurality of stationary radiation sources; and
   at least one scatter detector configured to receive a scattered beam formed by said primary beam interacting with the substance, said at least one scatter detector moveable with respect to said plurality of stationary radiation sources.

2. An imaging system in accordance with claim 1, further comprising a processor configured to activate said at least one stationary radiation source for an amount of time based on a distance between said at least one stationary radiation source and a centroid of the substance.

3. An imaging system in accordance with claim 1, further comprising a processor configured to activate said at least one stationary radiation source for an amount of time based on a distance between a centroid of the substance and said at least one scatter detector.

4. An imaging system in accordance with claim 1, wherein said plurality of stationary radiation sources are located within a first plane, said transmission detector is located within a second plane, and said at least one scatter detector is located within a third plane, wherein said first plane, said second plane, and said third plane are substantially parallel, and wherein said first plane is spaced a first distance from said second plane and spaced a second distance from said third plane.

5. An imaging system in accordance with claim 1, further comprising primary collimator configured to collimate said primary radiation beam generated by said at least stationary one radiation source, and said primary collimator configured to be stationary with respect to said at least one stationary radiation source.

6. An imaging system in accordance with claim 1, further comprising a guide rail, wherein said at least one scatter detector configured to move along said guide rail with respect to said plurality of stationary radiation sources.

7. An imaging system in accordance with claim 1, wherein said plurality of stationary radiation sources comprises a plurality of X-ray sources.

8. An imaging system in accordance with claim 1, wherein said least one stationary radiation sources is configured to generate a radiation beam that is incident on a container to generate said scattered beam, wherein said primary beam is detected by said transmission detector and said scattered beam is detected by said at least one scatter detector.

9. An imaging system in accordance with claim 1 further comprising:
   a processor configured to activate said at least one stationary radiation source when a portion of said at least one scatter detector is located at a line-of-sight passing through a centroid of the substance.

10. An imaging system in accordance with claim 9, wherein said plurality of stationary radiation sources are located within a first plane, said transmission detector is located within a second plane, and said at least one scatter detector is located within a third plane, wherein said first plane, said second plane, and said third plane are substantially parallel, and wherein said first plane is spaced a first distance from said second plane and spaced a second distance from said third plane.

11. An imaging system in accordance with claim 9, further comprising a primary collimator configured to collimate a radiation beam generated by said at least one stationary radiation source, and said primary collimator configured to be stationary with respect to said at least one stationary radiation source.

12. An imaging system in accordance with claim 9, wherein said at least one stationary radiation source is configured to generate a radiation beam that is incident on a container to output said primary beam and said scattered beam, said primary beam detected by said transmission detector and said scattered beam detected by said at least one scatter detector.

13. An imaging system for generating a diffraction profile of a substance, said imaging system comprising:
   a gantry fixedly coupled within said imaging system;
   a plurality of stationary radiation sources coupled to said gantry;

a transmission detector coupled to said gantry at a location to receive a primary beam generated by at least one stationary radiation source of said plurality of stationary radiation sources;

at least one scatter detector coupled to said gantry at a location to receive a scattered beam formed by said primary beam interacting with the substance, said at least one scatter detector moveable with respect to said plurality of stationary radiation sources; and a processor operatively coupled to said plurality of stationary radiation sources and configured to control at least said plurality of stationary radiation sources.

14. An imaging system in accordance with claim 13, wherein said plurality of stationary radiation sources comprises a plurality of X-ray sources.

15. An imaging system in accordance with claim 13, wherein said at least one stationary radiation source configured to generate a radiation beam that is incident on a container to generate said primary beam and said scattered beam, said primary beam detected by said transmission detector and said scattered beam detected by said at least one scatter detector.

16. An imaging system in accordance with claim 13, wherein said plurality of stationary radiation sources are located within a first plane, said transmission detector is located within a second plane, and said at least one scatter detector is located within a third plane, wherein said first plane said second plane, and said third plane are substantially parallel, and wherein said first plane is spaced a first distance from said second plane and spaced a second distance from said third plane.

17. An imaging system in accordance with claim 16, wherein said plurality of stationary radiation sources are positioned between said transmission detector and said at least one scatter detector.

* * * * *